US005830452A

United States Patent [19]
Bauer et al.

[11] Patent Number: 5,830,452
[45] Date of Patent: Nov. 3, 1998

[54] METHOD FOR ENHANCING THE ANTI-TUMOR THERAPEUTIC INDEX OF INTERLEUKIN-2

[75] Inventors: Robert J. Bauer, Lafayette; Jeffrey L. Winkelhake, San Diego; John D. Young, Lafayette; Robert Zimmerman, Orinda, all of Calif.

[73] Assignee: Chiron Corporation, Emeryville, Calif.

[21] Appl. No.: 273,364

[22] Filed: Jul. 11, 1994

Related U.S. Application Data

[63] Continuation of Ser. No. 615,964, Nov. 20, 1990, abandoned.

[51] Int. Cl.$^6$ .......................... A61K 45/05; A61K 38/20
[52] U.S. Cl. ........................................ 424/85.2; 530/351
[58] Field of Search .................... 424/85.1, 85.2; 530/351

[56] References Cited

U.S. PATENT DOCUMENTS

| | | | |
|---|---|---|---|
| 4,401,756 | 8/1983 | Gillis | 435/70.4 |
| 4,518,584 | 5/1985 | Mark et al. | 424/85.2 |
| 4,530,787 | 7/1985 | Shaked et al. | 530/351 |
| 4,569,790 | 2/1986 | Koths et al. | 530/351 |
| 4,572,798 | 2/1986 | Koths et al. | 530/351 |
| 4,604,377 | 8/1986 | Fernandes et al. | 424/85.2 |
| 4,624,661 | 11/1986 | Arimond | 604/151 |
| 4,637,834 | 1/1987 | Thurow | 106/156.4 |
| 4,656,132 | 4/1987 | Ben-Bassat et al. | 435/69.5 |
| 4,738,927 | 4/1988 | Taniguchi et al. | 435/243 |
| 4,748,234 | 5/1988 | Dorin et al. | 530/412 |
| 4,752,585 | 6/1988 | Koths et al. | 435/252.33 |
| 4,766,106 | 8/1988 | Katre et al. | 514/12 |
| 4,816,440 | 3/1989 | Thompson | 514/12 |
| 4,863,726 | 9/1989 | Stevens et al. | 424/85.2 |
| 4,885,164 | 12/1989 | Thurow | 424/85.4 |
| 4,894,226 | 1/1990 | Aldwin et al. | 424/85.2 |
| 4,902,501 | 2/1990 | Bandi et al. | 424/78.12 |
| 4,902,502 | 2/1990 | Nitecki et al. | 530/351 |
| 4,908,433 | 3/1990 | Mertelsmann et al. | 530/351 |
| 4,908,434 | 3/1990 | Mertelsmann et al. | 530/417 |
| 4,925,919 | 5/1990 | Mertelsmann et al. | 530/351 |
| 4,992,271 | 2/1991 | Fernandes et al. | 424/85.2 |
| 5,037,644 | 8/1991 | Shaked et al. | 424/85.2 |
| 5,078,997 | 1/1992 | Hora et al. | 424/85.2 |
| 5,102,872 | 4/1992 | Singh et al. | 514/21 |

FOREIGN PATENT DOCUMENTS

| | | |
|---|---|---|
| 88195 | 9/1983 | European Pat. Off. . |
| 91539 | 10/1983 | European Pat. Off. . |
| 92163 | 10/1983 | European Pat. Off. . |
| 94317 | 11/1983 | European Pat. Off. . |
| 109784 | 5/1984 | European Pat. Off. . |
| 268110 | 5/1988 | European Pat. Off. . |

OTHER PUBLICATIONS

Bauer et al., "Protein Drug Delivery by Programmed Pump Unfusion to Enhance the Therapeutic Index and to Aid in the Design of Next–Generation Drugs: Interleukin–2," in *Therapeutic Proteins–Pharmacokinetics and Pharmacodynamics,* Kung et al. (eds.), W.H. Freeman and Company, New York, pp. 239–253 (1993).

Bauer, et al., "Enhacement of Cytokine (IL–2_Therapeutic Ratio By Controlling Plasma Clearance Profiles" *FASEB J.,* 4(7), #1733 (A 1991).

Katre et al., "Chemical Modification of Interleukin 2 with Polymers: A Potent Drug–delivery System," In Marshak, D., and Liu, D., eds., *Therapeutic Peptides and Proteins,* Cold Spring Harbor Laboratory, Long Island, NY pp. 173–177 (1989).

Stoter et al., "Metastatic renal cell cancer treated with low–dose interelukin–2. A phase–II multicentre study," *Cancer Treatment Reviews* 16(A):111–113 (1989).

West et al., "Constant–Infusion Recombinant Interleukin–2 In Adoptive Immunotherapy of Advanced Cancer," *The New England Journal of Medicine,* 316(15):898–905 (Apr. 9, 1987).

Zimmerman et al. (1989, Dec. 1), Cancer Res. 49:6521–6528.

Vaage et al. (1987). Int. J. Cancer 39:530–533.

Lotze et al.(1986). Cancer 58:2764–2772.

Krigel et al.(1988, Jul. 1). Cancer Res. 48:3875–3881.

Talmadge et al.(1987) Cancer Res. 47:5725–5732.

Winkelhake et al.(1987) Cancer Res. 47:3948–3953.

Kohler et al.(1989) Cancer Investigation 7(3):213–223.

Hadden(1988) Cancer Detection & Prevention 12:537–552.

Abuchowski, et al. *Cancer Biochem.Biophys. 7*:175 (1984), "Cancer therapy with chemically modified enzymes I. Antitumor properties of polyethylene glycol–asparaginase conjugates".

Beauchamp, et al., *Anal.Biochem. 131*:25 (1983), "A new procedure for the synthesis of polyethylene glycol–protein adducts; effects on function, receptor recognition, and clearance of superoxide dismutase, lactoferrin, and $\alpha_2$ macroglobulin".

Davis, et al., *Biomedical Polymers,* Academic Press, New York, pp. 441–451 (1980).

Devos, *Nucl.Acids Res. 11*:4307 (1983), "Moleccular cloning of human interleukin 2 cDNA and its expression in *E.coli*".

Donohue, et al., *Cancer Res. 44*:1380 (1983), "In vivo administration of purified Jurkat–derived interleukin 2 in mice".

Donohue, et al., *J.Immunol. 130*:2203 (1983), "The fate of interleukin–2 after in vivo administration".

Gillis, et al.,*J.Exp.Med. 152*:1709 (1980), "Biochemical and biological characterization of lymphocyte regulatory molecules".

(List continued on next page.)

*Primary Examiner*—Ponnathapura Achutamurthy
*Attorney, Agent, or Firm*—Donald Pochopien; Philip L. McGarrigle; Robert P. Blackburn

[57] ABSTRACT

The present application relates to a method for enhancing the therapeutic index of a compound that is useful to treat tumors. More specifically, the present invention relates to a method for administering IL-2 to a tumor patient to maximize the therapeutic efficacy and minimize the toxicity.

29 Claims, 3 Drawing Sheets

OTHER PUBLICATIONS

Gillis, et al. *J.Immuol.* 124:1954 (1980), "Biochemical characterization of lymphocyte regulatory molecules".

Katre, et al., *Proc.Natl.Acad.Sci. (USA)* 84:1487 (1987), "Chemica;1 modification of recombinant interleukin 2 by polyethylene glycol increases its potency in the murine Meth A sarcoma model".

Knauf, et al., *J.Biol.Chem.* 263:15064 (1988), "Relationship of effective molecular size to systemic clearance in rat of recombinant interleukin–2 chemically modified with water–soluble polymers".

Matory, et al., *J.Biol.Resp.Mod.* 4:377 (1985), "Toxicity of recombinant human interleukin–2 in rats following intravenous infusion".

Mochizuki, et al., *J.Immunol.Meth.* 39:185 (1985), "Biochemical separation of interleukin–2".

Morgan, et al., *Science* 193:1007 (1976), "Selective growth of T lymphocytes from normal human bone marrow cells".

Morikawa, et al, *Cancer Res.* 47:37 (1987), "Enhancement of therapeutic effects of recombinant interleukin 2 on a transplantable rat fibrosarcoma by the use of a sustained relase vehicle, pluonic gel".

Nishimura, et al., *Cancer Immunol.Immunother.* 21:12 (1986), "Augmentation of the thrapeutic efficacy of adoptive tumor immunotherapy by in vivo administration of a slowly released recombinant interleukin 2".

Nishimura, et al., *J.Immunol.Meth.* 91:21 (1986), "Augmentation of the efficacy of adoptive immunotherapy with lymphokine–activated killer (LAK) cells".

Rosenberg, et al., *J.Exp.Med.* 161:1169 (1985), "Regression of established pulmonary metastases and subcutaneous tumor mediated by the systemic administration of high dose recombinant interleukin–2".

Taniguchi, et al., *Nature* 302:305 (1983), "Structure and expression of a cloned cDNA for human interleukin–2".

Watson, et al., *J.Exp.Med.* 150:849 (1979), "Biochemical and biological characterization of lymphocyte regulatory molecules".

Welte, et al., *J.Exp.Med.* 156:454 (1982), "Purification of human interleukin 2 to appartent homogeniety and its molecular heterogeneity".

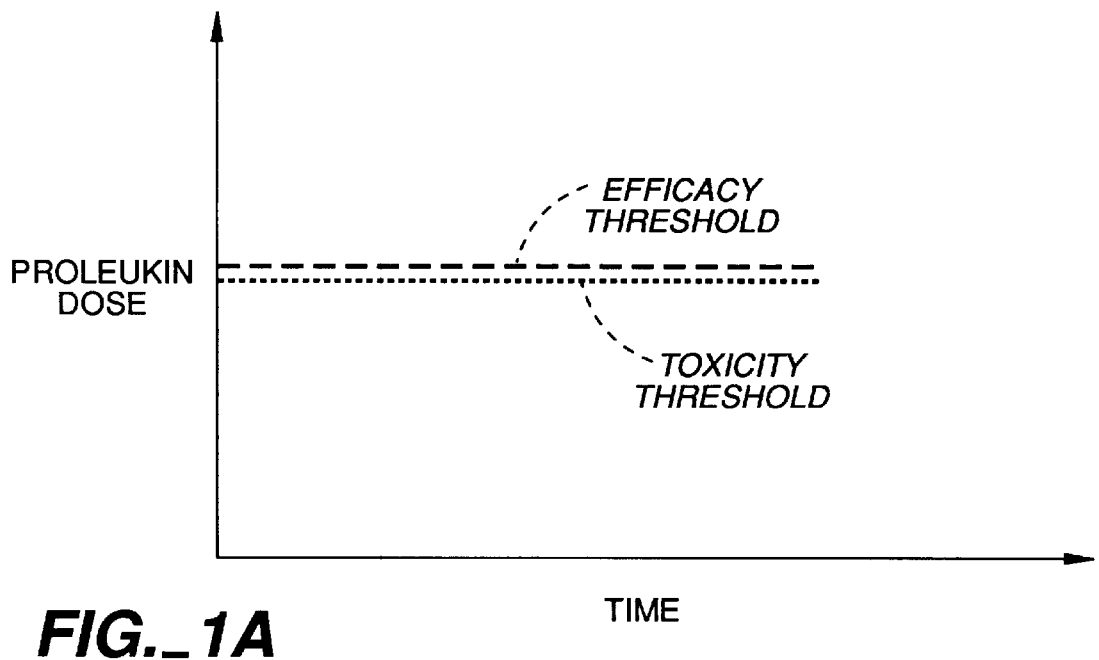
FIG._1A
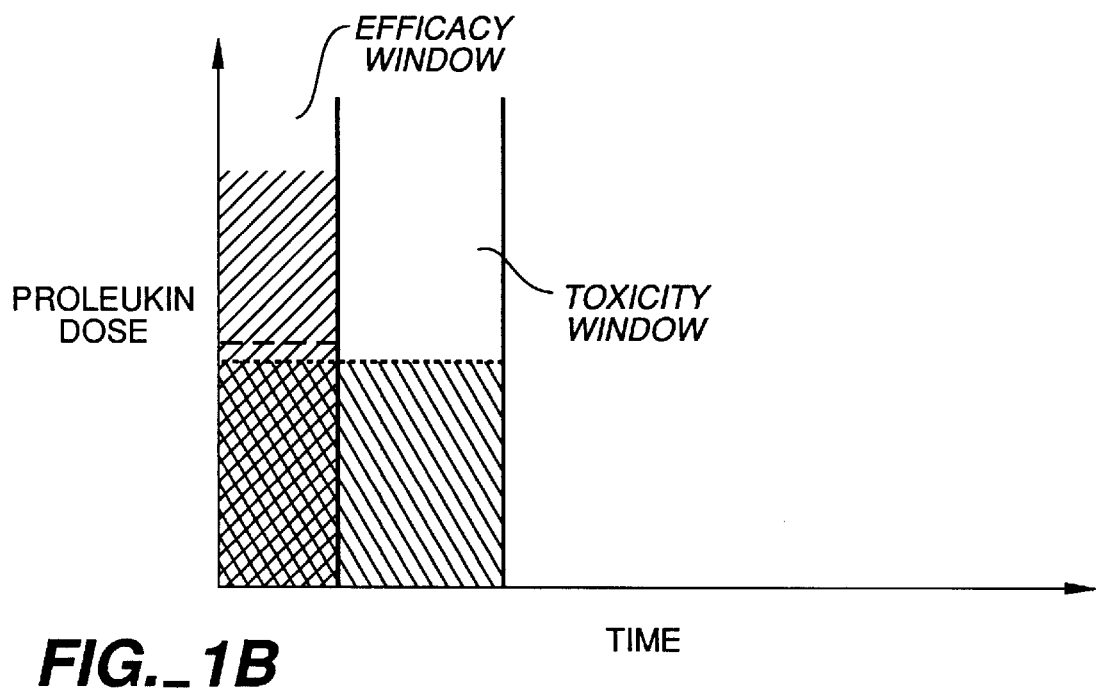
FIG._1B

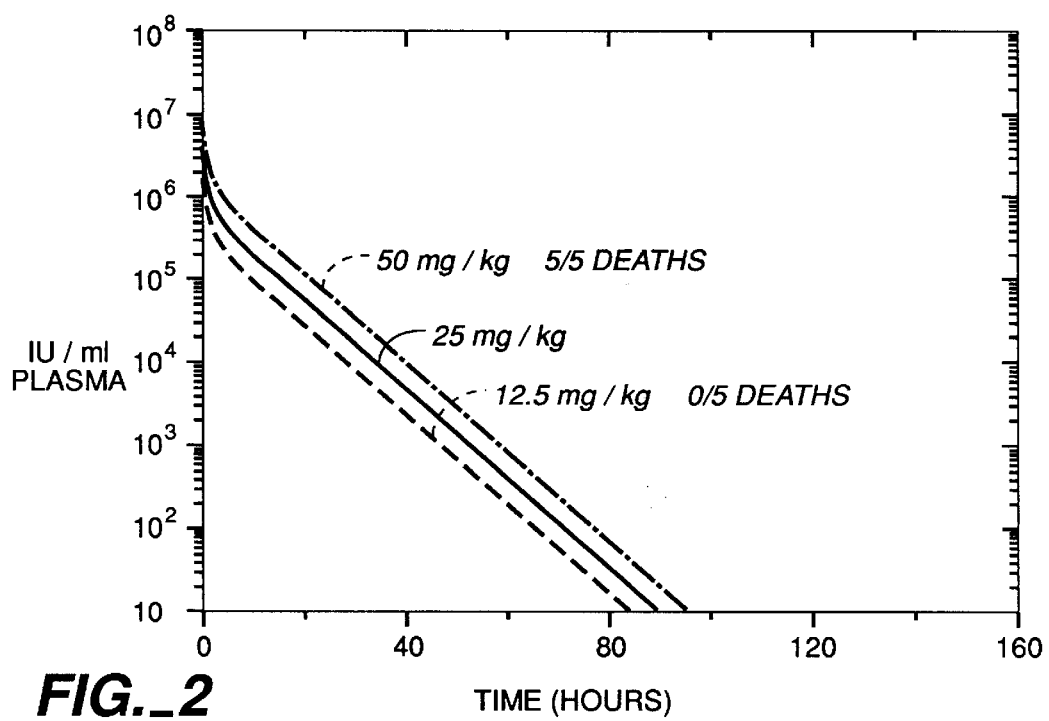
FIG._2
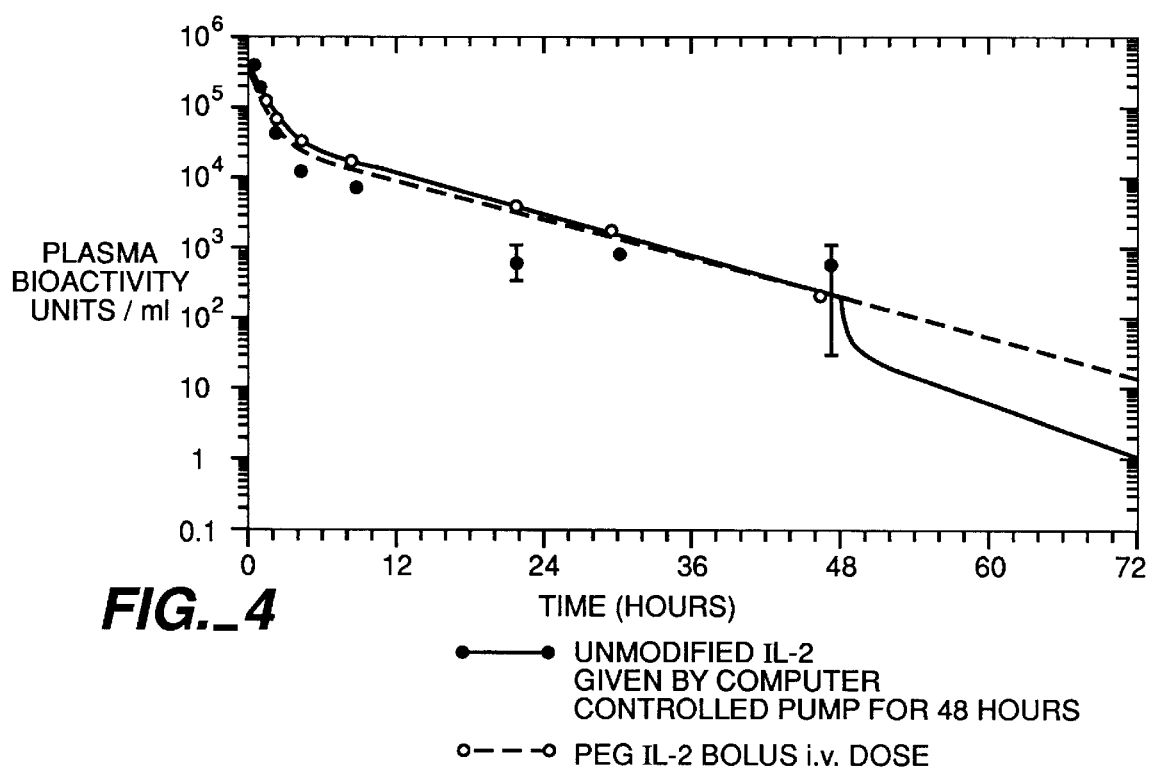
FIG._4

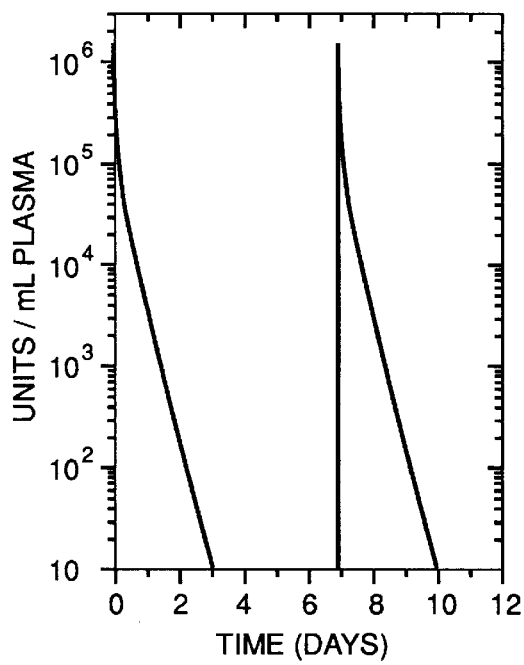
FIG._3A
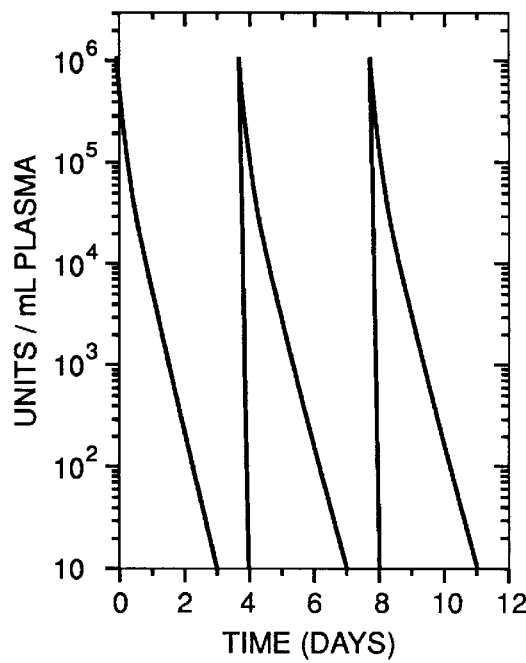
FIG._3B
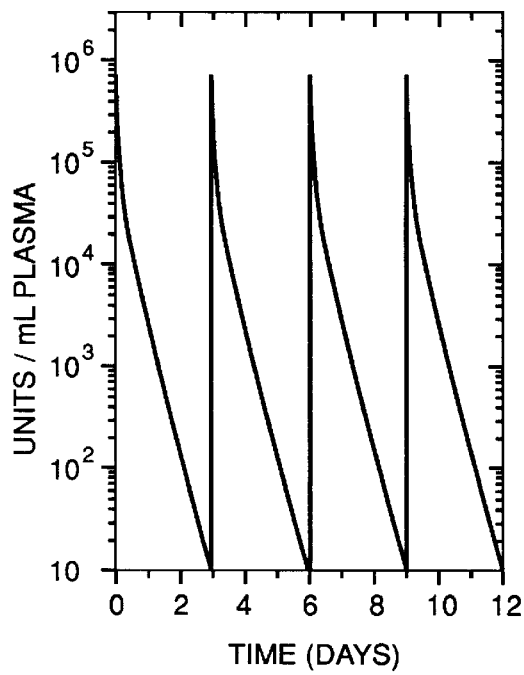
FIG._3C
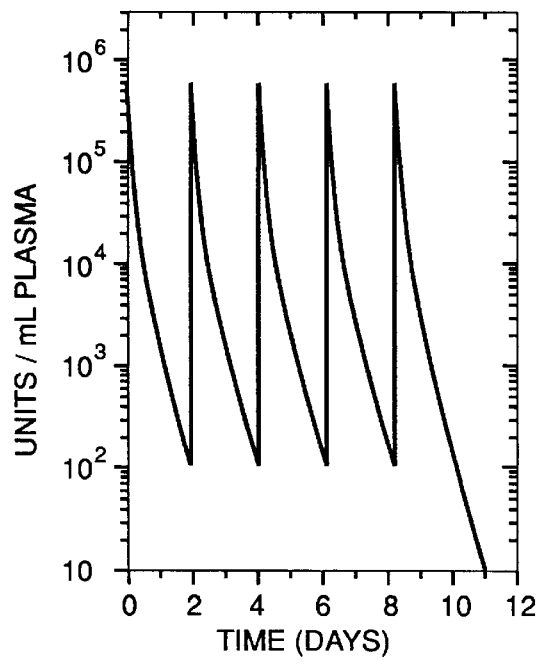
FIG._3D

METHOD FOR ENHANCING THE ANTI-TUMOR THERAPEUTIC INDEX OF INTERLEUKIN-2

This is a Continuation of U.S. application Ser. No. 07/615,964, filed Nov. 20, 1990, now abandoned.

FIELD OF THE INVENTION

The present application relates to a method for enhancing the therapeutic index of a compound that is useful to treat tumors. More specifically, the present invention relates to a method for administering IL-2 to a tumor patient to maximize the therapeutic efficacy and minimize the toxicity.

BACKGROUND OF THE INVENTION

Interleukin-2 (IL-2) is a lymphokine which is locally produced by normal peripheral blood lymphocytes in small quantities in response to various immunological stimuli. It induces the proliferation of antigen or mitogen stimulated T cells after exposure to plant lectins, antigens, or other stimuli. IL-2 was first described by Morgan, D. A., et al., *Science* (1976) 193:1007–1008 and originally called T cell growth factor because of its ability to induce proliferation of stimulated T lymphocytes. It is a protein with a reported molecular weight in the range of 13,000 to 17,000 (S. Gillis and J. Watson, *J. Exp. Med.* (1980) 159:1709) and has an isoelectric point in the range of 6–8.5. It is now recognized that in addition to its growth factor properties it modulates various in vitro and in vivo functions of the immune system. IL-2 is one of several lymphocyte-produced messenger-regulatory molecules that mediate cellular interactions and functions.

IL-2 was initially made by cultivating human peripheral blood lymphocytes (PBL) or other IL-2-producing cell lines, see, for example, U.S. Pat. No. 4,401,756, and Mertelsmann et al., European Patent Publication No. 92,163 and U.S. Ser. No. 603,580, filed Apr. 25, 1984. However, recombinant DNA technology has provided an alternative to PBLs and cell lines for producing IL-2. For example, Taniguchi, T., et al., *Nature* (1983) 302:305–310 and Devos, R., *Nucleic Acids Research* (1983)11:4307–4323 have reported cloning the human IL-2 gene and expressing it in microorganisms. Various muteins of IL-2 have been reported. For example, see U.S. Pat. No. 4,518,584, to Mark, et al. and U.S. Pat. No. 4,752,585, to Koths, et al.

Additionally, IL-2 can be modified with polyethylene glycol to provide enhanced solubility and an altered pharmokinetic profile (see U.S. Pat. No. 4,766,106 which is hereby incorporated by reference in its entirety).

Under normal physiologic conditions, IL-2 is thought to be both an autocrine and paracrine hormone which operates in localized areas of inflammation or immune reaction and is not measurable in the circulation. Therapeutic use of this lymphokine assumes benefit in the amplification of presumed insufficient immune mechanism(s) by administering IL-2 at pharmacologic doses rather than in reconstitution of an abnormal physiologic response (as is the case with insulin therapy). Pharmacologic characteristics of dose, route and schedule of administration become even more important than classically considered as a means of understanding efficacy.

Following i.v. administration to mice and rats, IL-2 disappears from the circulation with a pharmacokinetic profile of either a two or three-compartment model depending upon assay sensitivity. The first phase has a half-life of between 4 and 6 minutes—during which time approximately 75% of the dose disappears from the circulation. The secondary phase has a half life of between 2 and 4 hours—as does the major clearance phase seen with either i.p. or s.c. injections (Donohue & Rosenberg, 1983, *J. Immunol.*, 130:2203–2208; Donohue et al., 1984, *Cancer Res.*, 44:1380–1386; Matory et al., 1985, *J. Biol. Resp. Mod.*, 4 377–390).

Also, different IL-2 formulations have been used to alter the pharmacokinetic profile of IL-2. For example, three separate approaches have been taken to develop controlled or sustained release dosage forms of IL-2. In the first case, the lymphokine has been trapped in sustained release vehicles such as gelatin or a pluronic gel copolymer (Morikawa et al., 1987, *Cancer Res.*, 47:37–41). In the second case, mini-osmotic pumps have been implanted to provide a continuous infusion dosage form (e.g., Nishimura et al., 1986, *Cancer Immumol. Immunother.*, 21:12–18 and Nishimura et al., 1986, *J. Immunol. Met.*, 91:21–27). Finally, IL-2 has been "PEGylated" (Katre et al., 1987, *PNAS*, 84:1487–1491) and, as is seen with many other small proteins, covalent modification with polyethylene glycol enhances circulatory longevity (Davis et al., 1980, *BioMedical Polymers*, Academic Press, New York p. 441–451; Beauchamp et al., 1983, *Anal. Biochem.*, 131:25–33; Abuchowski et al., 1984, *Cancer Biochem. Biophys.*, 7:175–186). In the case of IL-2, this means decreasing the rate of clearance from the plasma, and thereby increasing the total area under the plasma curve by 15–20-fold. (Zimmerman et al., 1989, *Cancer Research*, 49:6521–6528).

A key factor affecting the efficacy of IL-2 is the dose intensity. Most investigators who used either i.p., i.v. or s.c. routes with low doses in the range of several hundred to several thousand IU saw little efficacy, although Vaage et al., 1987, *Int. J. Cancer*, 39:530–533 showed significant tumor growth inhibition at 100 IU when the IL-2 was administered s.c. around the tumor in a strongly immunogenic murine model. The first evidence that high dose IL-2 (15–20,000 IU/day) is more efficacious was obtained by Rosenberg et al., 1985, *J. Exp. Med.*, 161:1169–1188 who showed that thrice daily injections of doses totaling up to 18,000 I.U.s/day of IL-2 induced regression of metastases established 10 days prior to initiation of therapy in a methylcholanthrene-induced sarcoma, MCA-105. These types of animal models tend to over-optimistically suggest a potent therapeutic index for IL-2 because human tumors are not as immunogenic and because metastatic cancer is often not accessible to peritumoral injection. The models certainly suggest that the drug is potent if delivered directly to an immunogenic tumor.

The question of how often and how long to administer IL-2 has been a perplexing one since these early in vivo studies. The problem is characterized by a general lack of knowledge of the mechanisms involved in IL-2 pharmacodynamics. With these limited studies regarding IL-2 distribution, formulation, dose amount and schedule as a background, there is clearly a need to determine the dose, levels and proper schedule which will provide potent anti-tumor efficacy while being substantially nontoxic.

SUMMARY OF THE INVENTION

The present invention is a method for enhancing the therapeutic index of IL-2 treatment. The method is a manner of delivering IL-2 to a patient such that the IL-2 concentration in the patients' plasma follows a defined clearance profile. For example, we have found that the therapeutic index of IL-2 is tied to the peak, shape, trough level and duration of the curve for IL-2 plasma concentration. Initially, the patients' plasma IL-2 concentration is above the therapeutic dose level of IL-2, but less than the maximum tolerated dose. Over time, the IL-2 concentration is allowed to decline within defined parameters until it falls below detectable levels within 96 hours or less. This IL-2 plasma clearance-based treatment may be repeated, preferentially 7 days after the initial dose. The IL-2 can be unmodified, recombinant or natural human IL-2, or IL-2 may be modified with a polymer such as PEG, in order to produce a preferred clearance profile.

Among other factors, the present invention is the discovery that a specified clearance profile may affect toxicity when IL-2 is parenterally administered. This is advantageous because toxicity is a problem when IL-2 is given at large doses for the treatment of tumor growth.

BRIEF DESCRIPTION OF THE DRAWINGS

FIG. 1A, which is a plot of Proleukin (IL-2) dose versus time, shows the efficacy and toxicity thresholds of the peak/trough model.

FIG. 1B, which builds upon FIG. 1A and is a plot of Proleukin (IL-2) dose versus time, predicts that by manipulating IL-2 delivery (and attendant blood concentrations with time), it is possible to separate efficacy and toxicity to a greater extent than is possible without modifying IL-2 clearance from the plasma, thereby improving efficacy and reducing toxicity (increasing the therapeutic index).

FIG. 2 is a plot of concentration of PEG IL-2 in I.U./ml plasma in mice versus time (hours) for three different dosages of IL-2 given as a single iv bolus.

FIGS. 3 A, B, C, and D show the simulations of PEG-IL-2 in mice dosed i.v. with 25 mg/kg total dose on the four schedules studied in the Meth A tumor model.

FIG. 4 shows the blood clearance curves for PEG-IL-2 and IL-2 infused by computer program-driven pump for 48 hours.

DETAILED DESCRIPTION OF THE INVENTION

The invention described herein draws on previous work by us and others in the field. By way of example, such work consists of scientific papers, patents or pending patent applications. All of these publications and applications, cited previously or below are hereby incorporated by reference in their entireties.

In the present invention, we have found that the optimal dose and schedule for delivery of IL-2 is described by blood concentration multiplied by time thresholds such that certain blood concentrations define the level required for maximal anti-tumor efficacy and other blood concentrations define the level required to minimize toxicity. The principle can be described by a peak/trough model where IL-2 blood concentration is varied to achieve the goals described above. The threshold components of the peak/trough model are shown in FIG. 1A. Our model is uniquely different from those describing standard therapeutic ratios because of the separation of anti-tumor efficacy and toxicity thresholds with time-windows. In the peak/trough model, threshold blood concentration and the period of time-above and time-below threshold (e.g., the shape of that curve over a 24–48 hour period) are proposed to be crucial to initiating mechanism(s) of IL-2 action. As depicted schematically in FIG. 1B, the peak/trough model predicts that, by manipulating IL-2 delivery and attendant blood concentrations with time, it should be possible to separate efficacy and toxicity to a greater extent than is possible by standard bolus dosing or infusion dosing regimens, thereby improving efficacy and reducing toxicity (increasing the therapeutic index). Because the host's response to IL-2 plays a major role in the efficacy and toxicity, this model of peak/trough delivery of IL-2 is also key to initiating the pharmacodynamic effects of IL-2.

The basic components of the peak/trough model served as one of the tools with which we developed a second generation product, namely polyethylene glycol modified IL-2 (PEG-IL-2). (Polymer modified IL-2 has a longer in vivo half life than unmodified IL-2, see U.S. Pat. No. 4,766,106). With the subsequent availability of PEG-IL-2, the foundation of the concept was solidified in preclinical studies comparing anti-tumor responses and pharmacokinetic parameters of half-life and area under the blood concentration curve for PEG-IL-2 and IL-2. In murine tumor studies, Zimmerman et al., Cancer Research, 49:6521–6528 (1989) (which is incorporated by reference in its entirety) showed enhanced anti-tumor activity with PEG-IL-2 being approximately 24-fold more active than IL-2 on a dose per dose basis. It was clear from these studies that the therapeutic index of IL-2 (its efficacy and toxicity) is related to both the blood concentration multiplied by the time curve and the total delivered dose of IL-2.

The artisan of ordinary skill understands that a blood concentration curve in an organism is based upon the measurement of blood concentration of IL-2 as a function of time, wherein the resulting curve reflects the IL-2 clearance profile of the organism; that the area under the blood concentration curve is a quantitative determination made from the blood concentration curve and further reflects the IL-2 clearance profile; and that the "blood concentration multiplied by the time curve" is a description of the calculation one performs to determine the area under the blood concentration curve for a particular time segment ($\Delta$time). The skilled artisan further understands that various mathematical methods, including analytical calculus, may be employed to determine the area under a particular curve to a desired level of precision.

In our studies we have discovered that there are different time and threshold components which define the invention. For example, to achieve efficacy, the IL-2 blood level must be above a specific level for a specific time, and the blood level must be below a certain level within a specific time and for a specific time (there must be a "drug holiday"). Specifically, the peak height of IL-2 blood concentration does little to contribute to toxicity, the shape of the clearance curve is more important. The peak height contributes to anti-tumor effects, i.e., efficacy is dose dependent. Furthermore, we have found that trough levels for IL-2 blood concentrations are important. For example, higher trough levels or shorter rests between doses contribute to greater toxicity.

As stated above, the blood level must go above a specific threshold. This threshold is the baseline necessary for efficacy and can be as high as is tolerated by the patient. For example, the physician's observations may set the maximum tolerated dose (MID) based on observable signs of toxicity, such as nausea, hypotension, weight gain, fever, etc. Since the disease being treated is typically fatal, it is important to administer as much IL-2 as can be tolerated so that maximum efficacy is possible. This threshold may vary from patient to patient, however, the MTD for a single dose of unmodified IL-2, irrespective of any other dose is typically from 5 to 10 million I.U./kg. The maximum tolerated dose for an i.v. polyethylene glycol modified IL-2 of approximately 160 kD apparent molecular weight is between 16 and 18 million I.U./kg. When polyethylene glycol modified IL-2 is administered s.c. a local reaction (redness and inflammation) is observed at approximately 3.6 million I.U./kg. The MID for Q 8 hours, for 1–5 days (14 total doses in which each dose is delivered by a 15 minute infusion) is approximately 720,000 and 800,000 I.U./kg. Furthermore, we have found that it is important to keep the blood level above the threshold for a specific length of time. This time is preferably between 12 hours and 80 hours, more preferably between 24 and 60 hours.

Additionally, the drug must be below a certain level by a certain time before the next dose is given. The blood level is preferably below 10 I.U./ml plasma, more preferably below 1 I.U./ml plasma, most preferably it is substantially eliminated. The specific time may vary from patient to patient, however, it is generally between 48 and 96 hours. (For example, see FIG. 2, which shows that when PEG-IL-2 is cleared after 82 hours 0/5 mice die, but if the IL-2 is not cleared until 96 hours then 5/5 mice die.)

Also, the IL-2 blood concentration must be below the level mentioned above for a defined time ("drug holiday") to allow the patient to "recover" from the undesirable effects of IL-2. In our studies with experimental animals we have found that 2½ to 3 days is necessary. However, we have found that it is necessary to provide a longer holiday for humans. Preferably, this holiday is between 3½ and 4½ days between dosing regimens. Thereafter, a new schedule of IL-2 dosing may be administered to provide the immune system with another boost.

Due to these factors, it is preferable to administer IL-2 at the MTD and maintain the blood concentration above 100 I.U./ml for at least 48 hours and then to keep the IL-2 blood level below 1 I.U./ml plasma for at least 3½ days before the cycle is repeated.

The following examples illustrate different pharmokinetic profiles that achieve the goals of the present invention. However, it should be appreciated that these specific profiles may be adjusted or modified to further define the maximum and minimum IL-2 concentrations at various times which achieve a similar effect. For example, the upper limit of the curve, defined by the MTD, can be determined as described above, and the lower limit of the curve can be determined by the level at which there is an unacceptable therapeutic response. Likewise, the time periods defined above can be determined by a person of ordinary skill in the art For example, the time for realizing a beneficial effect can be determined by varying the IL-2 blood concentration around the specific parameters described here in the text and the examples. This time can be shortened until there is no beneficial effect or it can be lengthened until toxicity occurs. Furthermore, the "drug holiday" can be varied around the specific times shown herein by observing its effect on toxicity and efficacy. These manipulations are within the skill of a routineer in the art given the teachings in this specification.

Once an optimum pharmokinetic curve is described, the attending physician can administer IL-2 by bolus dose, continuous infusion, or constant infusion (infusion for a short period of time, i.e. 1–6 hours). The IL-2 can be administered intravenously, subcutaneously, intraperitoneally, etc. Furthermore, IL-2 can be administered by a computer driven pump that can be programmed with various instructions to achieve a precise pharmokinetic curve. An example of a preferred computer program is shown in R. Bauer, PUMP and INFUN Programs, Copyright Registration No. TX4 464–741 which is hereby incorporated by reference in its entirety. A feedback sensor/mechanism may also be employed to monitor the IL-2 blood level so that the level can be adjusted by the pump or other means.

I. IL-2 Background Information

IL-2 can be produced by a prokaryotic microorganism or an eukaryotic cell that has been transformed with a native or modified human IL-2 DNA sequence. It has hydrophobic and hydrophilic regions, and is unglycosylated when produced in E. coli. The IL-2 DNA useful in the present invention encodes a protein having: (a) an amino acid sequence that is essentially identical to the amino acid sequence of native human IL-2, including the disulfide bond to the cysteines at positions 58 and 105, and (b) has biological activity that is similar to native human IL-2. Substantial identity of amino acid sequences means the sequences are identical or differ by one or more amino acid alterations (deletions, additions, substitutions) that do not cause an adverse functional dissimilarity between the synthetic protein and native human interleukin-2. Examples of such proteins see: European Patent Application No. 83101035.0 filed Feb. 3, 1983 (published Oct. 19, 1983 under Publication No. 91539); European Patent Application No. 82307036.2 filed Dec. 22, 1982 (published Sep. 14, 1983 under No. 88195); the recombinant IL-2 muteins described in European Patent Application No. 83306221.9 filed Oct. 13, 1983 (published May 30, 1984 under No. 109748) which is the equivalent to Belgian Patent No. 893,016, commonly owned U.S. Pat. No. 4,518,584, and the recombinant IL-2 described in this application.

The precise chemical structure of IL-2 depends on a number of factors. As ionizable amino and carboxyl groups are present in the molecule, a particular protein may be obtained as a acidic or basic salt, or in neutral form. All such preparations which retain their activity when placed in suitable environmental conditions are included in the definition of proteins herein. Further, the primary amino acid sequence of the protein may be augmented by derivitization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of protein herein so long as the activity of the protein is not destroyed. It is expected that such modifications may quantitatively or qualitatively affect the activity, either by enhancing or diminishing the activity of the protein, in the various assays. Further, individual amino acid residues in the chain may be modified by oxidation, reduction, or other derivatization, and the protein may be cleaved to obtain fragments which retain activity. Such alterations which do not destroy activity do not remove the protein sequence from the definition of IL-2 herein.

Finally, modifications to the primary structure itself, by deletion, addition, or alteration of the amino acids incorporated into the sequence during translation, can be made without destroying the activity of the protein. For example, at least one cysteine residue which is: not essential to biological activity; is present in the biologically active protein; and is free to form a disulfide link, may be deleted or replaced with a conservative amino acid to eliminate sites for intermolecular crosslinking or incorrect intramolecular disulfide bond formation. Such modified proteins, known as "muteins", are described in U.S. Pat. Nos. 4,518,584 issued May 21, 1985 and 4,752,585 issued Jun. 4, 1988. A conservative amino acid alteration in this context is defined as one which does not adversely affect biological activity and involves substitutions or deletion of the cysteine at position 125 or at position 104 (numbered in accordance with the native molecular). The preferred conservative amino acids that are useful to replace cysteine are: serine, alanine, threonine, glycine, valine, leucine, isoleucine, tyrosine, phenylalanine, histidine, and tryptophan. The preferred conservative amino acids that are useful to replace methionine are the same as for cysteine with the addition of asparginine and glutamine, but exclude histidine and tryptophan. A preferred IL-2 mutein has the cysteine at position 125 replaced with a serine residue and/or the methionine at amino acid position 104 replaced with an alanine residue. Other preferred IL-2 muteins include those which have as many as six N-terminal deletions. For example, des-Ala$_1$ des-Pro$_2$ des-Thr$_3$ des-Ser$_4$ des-Ser$_5$ des-Ser$_6$ IL-2 is an N-minus six mutein, other muteins may have fewer amino acid deletions. Specifically preferred muteins are des-Ala$_1$ des-Pro$_2$ des-Thr$_3$ des-Ser$_4$ Ala$_{104}$ Ser$_{125}$ IL-2 and Ala$_1$ Ser$_{125}$ IL-2, to name a few.

As mentioned previously, recombinant IL-2 can be produced by prokaryotic microorganism or eukaryotic cells. Preferably, the IL-2 is produced by transforming a prokaryotic microorganism with DNA to produce a protein that possesses native human IL-2 activity. Examples of transformed microorganisms are described in the European patent applications and U.S. patents noted above. Bacteria are preferred prokaryotic microorganisms for producing IL-2 and *E. coli* is especially preferred. A typical transformed microorganism useful in the present invention is *E. coli* K-12, strain MM294, transformed with plasmid pLW1 (deposited at the American Type Culture Collection on Aug. 4, 1983 by Cetus Corporation under the provisions of the Budapest Treaty and having accession No. 39,405). Synthetic recombinant IL-2 can also be made in eukaryotes, such as yeast or human cells.

Processes for growing, harvesting, disrupting, or extracting the IL-2 from cells are substantially described in U.S. Pat. Nos. 4,604,377; 4,738,927; 4,656,132; 4,569,790; 4,748,234; 4,530,787; 4,572,298; U.S. Ser. Nos. 167,144; 48,408 and (Cetus case 2197.2, filed May 31, 1988) which are hereby incorporated by reference in their entireties. Other procedures for purifying native IL-2 from T cells are described by Watson, J. et al., *J. Exp. Med.* (1979) 150:849–861; Gillis, S., et al., *J. Immunology* (1980) 124:1954–1962; Mochizuki, D. Y., et al., *J. Immun Meth.* (1980) 39:185–201; Welte, K., et al., *J. Exp. Med.* (1982) 156:454–464; and European Patent Applications 83103582.9 (published Oct. 26, 1983 under No. 92163 and 83400938.3 published Nov. 16, 1983 under No. 94317) which are also incorporated by reference in their entireties.

After the IL-2 is produced and purified it may be incorporated into a pharmaceutical composition for application in human and veterinary therapeutics, such as cancer therapy and the treatment of infectious diseases. As composition, it is parenterally administered to the subject by methods known in the art. This composition may contain other compounds that increase the effectiveness or promote the desirable qualities of IL-2. The composition must be safe for administration via the route that is chosen, it must be sterile, retain bioactivity, and it must stably solubilize the IL-2. To maintain the sterility and to increase the stability of IL-2, the composition is lyophilized and reconstituted prior to use.

Formulations that are useful in the present method are shown in various patents and publications. For example, U.S. Pat. No. 4,604,377 shows a preferred IL-2 formulation which has a therapeutic amount of IL-2, which is substantially free from non-IL-2 protein and endotoxin, a physiologically acceptable water soluble carrier, and a sufficient amount of a surface active agent to solubilize the IL-2, such as sodium dodecyl sulfate. Other ingredients can be included, such as sugars. U.S. Pat. No. 4,766,106 shows formulations including polyethylene glycol (PEG) modified IL-2. European patent application, Publication No. 268,110, shows IL-2 formulated with various non-ionic surfactants selected from the group consisting of polyoxyethylene sorbitan fatty acid esters (Tween-80), polyethylene glycol monostearate, and octylphenoxy polyethoxy ethanol compounds (Triton X405). U.S. Ser. No. 775,751 discloses IL-2 formulations comprising human serum albumin and U.S. Ser. No. 339,971 discloses IL-2 formulations comprising human serum albumin and amino acids. All of the above patents and patent applications are hereby incorporated by reference in their entireties.

II. Polymer Modified IL-2

Polymer modified IL-2 is useful because it has an increased in vivo half life, reduced immunogenicity and increased solubility. Most importantly, the modification regulates the in vivo clearance so that the IL-2 blood level can be regulated in accordance with the present invention. (Unmodified IL-2 is cleared quickly from the body if it is given in a bolus dose. The present curve would be difficult to achieve if the IL-2 is cleared too quickly). For example, an attending physician can manipulate the size of the polymer modified IL-2 so that the IL-2 blood concentration will be maintained within the optimum curve as described above and in the examples. In this invention it is not the polymer that is advantageous, it is simply a mechanism to achieve the appropriate IL-2 curve.

In a preferred aspect of the present invention, purified IL-2 is covalently conjugated to a homopolymer of polyethylene glycol (PEG) or a polyoxyethylated polyol (POP). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the IL-2. However, it will be understood that the type and amount of the reactive groups may be varied to achieve a covalently conjugated PEG/IL-2 of the present invention.

Water soluble polyoxyethylated polyols are also useful in the present invention. They include polyoxyethylated sorbitol, polyoxyethylated glucose, polyoxyethylated glycerol (POG), etc.; POG is preferred. One reason is that the glycerol backbone of polyoxyethylated glycerol is the same that occurs in mono, di-, triglycerides commonly found in animals and humans. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070. PEG/IL-2 and POG/IL-2 conjugates are further disclosed in U.S. Pat. No. 4,766,106, which is hereby incorporated by reference in it's entirety along with Knauf et al.

The following discussion is directed to the conjugation of these water soluble polymers to IL-2. It should be understood that even though PEG or POG is mentioned, other water soluble polymers can be used.

The PEG or POG is attached to IL-2 by covalent conjugation. "Covalently conjugated" or "conjugated" refer to the covalent linking of PEG or POG to IL-2 via an activated PEG or POG. "Active" or "activated" describes the attachment of a reactive group onto a PEG or POG hydroxyl (-OH) group, so that they can be conjugated to IL-2. Generally, the PEG or POG molecule is activated by attaching the reactive group to a hydroxyl group and then the active molecule is covalently conjugated to an amino group or IL-2. While conjugation may occur between any reactive amino acids on the protein, the reactive amino acid is preferably lysine. The lysine is linked to a reactive group on PEG or POG through its free-amino group.

Processes for covalently conjugating IL-2 to a polymer are described in U.S. Pat. Nos. 4,902,501 and 4,766,106, both of which are hereby incorporated by reference in their entireties. For example, U.S. Pat. No. 4,902,502 describes a process for linking a polymer to IL-2 via a urethane or carbamate bond. U.S. Pat. No. 4,766,106 describes covalent conjugation between a polymer and IL-2 through an ester or amide bond (see column 9, line 38, to column 10, line 23). The reaction conditions during the covalent conjugation are also included in those patents referenced above. For example, the molar ratio of activated polymer molecules per mole IL-2 is shown in both references. However, this ratio does depend on the percent activity of the activated polymer. Preferred pH ranges are also disclosed in those references. For example, a pH range from about 5 to 9 is preferred in the '106 patent, whereas a pH range between 8 and 10 is preferred in the '502 patent. Other parameters such as reaction time, buffers, purification procedures, characterization procedures, assay procedures, and formulations are further disclosed in these two references and are incorporated by reference as discussed above.

III. Formulations

The polymer modified IL-2 or the unmodified IL-2 can be formulated for parenteral administration. For example, see U.S. Ser. No.775,751, wherein IL-2 is formulated at physiological pH using serum albumin; U.S. Pat. No. 4,816,440, wherein IL-2 can be formulated with sodium laureate; U.S. Pat. No. 4,605,377, wherein IL-2 can be formulated with a water soluble carrier such as mannitol and sodium dodecyl sulfate; U.S. Pat. No. 4,894,226, wherein IL-2 can be connected to a flexible spacer and a polyproline molecule; U.S. Ser. No.101,175; wherein IL-2 can be formulated with various nonionic surfactants; U.S. Ser. No. 231,757, wherein polymer modified IL-2 is formulated in a controlled release formulation, including a polylactide co-glycoside polymer and human serum albumin; U.S. Ser. No. 373,928, which discloses IL-2 in combination with a cyclodextrin; and U.S. Ser. No. 467,807, which discloses purified albumin formulations which may include IL-2. These patents and patent applications are hereby incorporated by reference in their entireties.

Various compounds can be added as stabilizers for IL-2. "Stabilizer" is defined as an amino acid, vitamin, polymer, fatty acid, or a salt of a low molecular weight organic acid which will cause IL-2 to remain stably soluble in an aqueous solution or after lyophilization and reconstitution. Some of these stabilizers exist in the body and many have a history of being injected into humans. Thus, they may be considered relatively safe because they do not present the same toxicity problems as do other formulants.

Preferred amino acids are the levo rotatory (L) forms of carnitine, arginine, and betaine, more preferred amino acid stabilizers are arginine, or a mixture of arginine and carnitine, the most preferred amino acid stabilizer is a mixture of carnitine and arginine. A preferred vitamin is pyridoxin ($B_6$), preferably as a hydrochloride salt, either alone or in combination with the amino acids. A preferred polymer is polyvinylpyrrolidone (PVP) with an average molecular weight between 2,000 and 3,000, more preferably about 2,500; or polyethylene glycol (PEG) with an average molecular weight between 3,000 and 5,000, more preferably about 4,000. Polymers outside of these ranges do not work as satisfactorily. A preferred fatty acid is capric acid and a preferred salt of a low molecular weight organic acid is succinic acid. More preferably these acids are sodium salts.

The pH of the combination is preferably adjusted to between 5.0 and 8.5 before adding the IL-2, more preferably between 6.0 and 8.0, most preferably between 6.0 and 7.5. When carnitine is used singly to stabilize IL-2, the solution pH will be approximately 3 to 3.5. Consequently, it is preferred to include an additional factor such as serum albumin. The serum albumin may be derived from humans, pigs, cows, and the like. Similarly, when arginine is used alone to stabilize IL-2 the solution pH may be between 9.5 and 10.5. A mixture of arginine and serum albumin (before IL-2 addition) within the pH range of 6 to 8.5 would give a pharmaceutically acceptable formulation. When both arginine and carnitine are used as the stabilizer, it is preferred to mix them together to bring the pH into a range between 5.0 and 8.5, more preferably between 6.0 and 8.0, most preferably between 6.0 and 7.5 before adding the IL-2. This combination is most preferred.

Typically, the stabilizer concentration is between 0.1 and 10 w/v %, more preferably between 0.25 and 4.5 w/v %. Each component is expressed in terms of its weight versus the final liquid volume). When either arginine, carnitine, or betaine is used individually their concentrations are between 0.1 and 5.0 w/v %, more preferably between 0.2 and 3.0 w/v %. When arginine and carnitine are mixed together their individual concentrations are also in this range. The ratio between arginine and carnitine is preferably between 0.8 and 1.0, more preferably between 0.85 and 0.90. When serum albumin is used its concentration is between 0.25 and 5.0 w/v %, more preferably between 0.5 and 3.0 w/v %. The preferred vitamin, polymer, or fatty acid concentration is between 0 and 10 w/v %, more preferably between 1 and 5 w/v, most preferably between 1 and 3%. The preferred concentration of the salt of a low molecular weight organic acid is between 0 and 1M, more preferably between 0.05 and 0.5M, most preferably between 0.1 and 0.3M.

Sugars or sugar alcohols can be included in the IL-2 compositions. Sugar is defined as mono, di, or polysaccharides, or water-soluble glucans, including for example fructose, glucose, mannose, sorbose, xylose, maltose, lactose, sucrose, dextran, pullulan, dextrin, cyclodextrin, soluble starch, hydroxyethyl starch, and carboxymethylcellulose-Na. Sucrose is the most preferred Sugar alcohol is defined as a $C_4$–$C_8$ hydrocarbon having an -OH group and includes for example mannitol, sorbitol, inositol, galactitol, dulcitol, xylitol and arabitol; mannitol is the most preferred The sugars or sugar alcohols mentioned above may be used individually or in combination. There is no fixed limit to the amount used, as long as the sugar or sugar alcohol is soluble in the aqueous preparation. Preferably, the sugar or sugar alcohol concentration is between 1.0 w/v % and 7.0 w/v %, more preferably between 2.0 and 6.0 w/v %.

It is also preferred to use a buffer in the composition to minimize pH changes in the solution before lyophilization or after reconstitution. Most any physiological buffer may be used, but citrate, phosphate, succinate, or glutarate buffers, or mixtures thereof are preferred. Most preferred is a citrate buffer. Preferably, the concentration is from 0.01 to 0.3M.

IV. Administration

The IL-2 can be given by any acceptable route or schedule such that the IL-2 blood concentration clearance pattern is consistent with that defined in the present invention.

As is the case for many proteins, it is preferable to administer IL-2 with a carrier to prevent non-specific adhesion of IL-2 to plastic or glass surfaces, especially at lower IL-2 concentrations (i.e., <50 µg/ml total protein). Accordingly, we prefer to co-administer IL-2 with such a carrier, which can be present in the formulation or added during administration. Preferable carriers have been mentioned above and include HSA or non-ionic surfactants. See U.S. Pat. Nos. 4,637,834 and 4,885,164 which are hereby incorporated by reference in their entireties. Also, various equipment and techniques that are known to those of skill in the art can be employed to minimize this effect.

The present process will now be illustrated by reference to the following examples which set forth particularly advantageous embodiments. However, it should be noted that these embodiments are illustrative and are not to be construed as restricting the invention in any way.

The following examples are illustrative of this invention. They are not intended to be limiting upon the scope thereof.

EXAMPLE 1

Unmodified IL-2 and PEG modified IL-2 were administered to mice who were transplanted with a Meth A tumor. The technical details for the materials and methods are similar to those specifically set out in Zimmerman et al., 1989, *Cancer Research*, 49:6521–6528 which is hereby incorporated by reference in its entirety.

The purpose of this experiment was to define the peak height and shape of the IL-2 blood concentration curve. Unmodified IL-2 (IL-2) and PEG modified IL-2 (having apparent molecular weights of 95 kD and 160 kD) were given to the mice in one bolus dose. Unmodified IL-2 is cleared quicker than the 95 kD PEG-IL-2, which is cleared quicker than the 160 kD PEG-IL-2. Consequently, one can determine the effect of dose and duration by administering IL-2 and PEG-IL-2 molecules that will remain in the body for varying lengths of time. The doses and the results are shown in Table 1 below.

TABLE 1

| Group | Dose | No. Deaths/No. Treated | % TGI | Cures |
|---|---|---|---|---|
| IL-2 | 75 mg/kg | 0/5 | 56% | 0/5 |
| 95 kD PEG IL-2 | 60 mg/kg | 0/5 | 93% | 3/5 |
| 160 kD PEG IL-2 | 50 mg/kg | 5/5 | — | — |
| 95 kD PEG IL-2 | 48 mg/kg | 0/5 | 82% | 0/5 |
| 160 kD PEG IL-2 | 25 mg/kg | 2/5 | 35% | 0/3 |
| 95 kD PEG IL-2 | 24 mg/kg | 0/5 | 46% | 0/5 |
| IL-2 | 22.5 mg/kg | 0/5 | 21% | 0/5 |

* Peak height alone contributes little to toxicity of IL-2 in Meth A model
* Shape of clearance curve is important Consequently, it is apparent that doses of up to 75 mg/kg IL-2 and up to 60 mg/kg 95 kD PEG-IL-2 are not toxic. Furthermore, these doses are efficacious to varying levels. However, it is apparent that doses of IL-2 that remain in the body for longer periods (using the 160 kD PEG-IL-2 molecule) are toxic at different doses without being very effective.

Another experiment was performed to determine the effect of IL-2 peak serum concentration on therapeutic index. 160 kD PEG-IL-2 was administered concurrently with IL-2 at the doses indicated below in Table 2. It is apparent that there is no increase in lethality with greater peak heights.

TABLE 2

| Group (mg/kg) | Δ Body Weight | Deaths | % TGI | Cures |
|---|---|---|---|---|
| PEG 25 + | 1.02 | 0/10 | 99.6 | 6/10 |
| 12.5 IL-2 + | 1.03 | 0/10 | 98.8 | 5/10 |
| 7.5 IL-2 | 1.00 | 0/10 | 99.7 | 8/10 |
| PEG 12.5 + | 1.05 | 0/10 | 99.7 | 7/10 |
| 12.5 IL-2 + | 1.01 | 0/10 | 99.8 | 10/10 |
| 7.5 IL-2 | 1.03 | 0/10 | 97.2 | 7/10 |
| 12.5 IL-2 Alone | 1.08 | 0/10 | 54.2 | 0/10 |
| Controls | 1.20 | 0/10 | — | — |

* PEG-IL-2: 25 mg/kg (75 mg/m$^2$) or 12.5 mg/kg (37.5 mg/m$^2$) total dose i.v., Q7D × 2.
* Proleukin: 12.5 mg/kg (37.5 mg/m$^2$) or 7.5 mg/kg (22.5 mg/m$^2$) given simultaneously with PEG-IL-2.

An experiment was performed to determine how the drug holiday affected the IL-2 toxicity. IL-2 was continuously administered to mice at either of two dose levels. Bolus IL-2 doses were administered (i.v.) to these mice to elevate their IL-2 blood concentration above the continuous infusion level. This administration schedule creates blood concentration peaks, but without the troughs. It is apparent from Table 3 that a drug holiday is necessary to reduce toxicity.

TABLE 3

| Group | No. Deaths/No. Treated | % TGI | Cures |
|---|---|---|---|
| CI 0.57 mg/kg + | 0/5 | 49% | 0/5 |
| IV 5 mg/kg | 2/5 | 90% | 1/3 |
| CI 0.28 mg/kg + | 0/5 | 55% | 0/5 |
| IV 5 mg/kg | 3/5 | 83% | 1/2 |
| IV 5 mg/kg | 0/5 | 88% | 0/5 |

* No drug holiday period increases IL-2 toxicity in the Meth A model.
* Seven day i.p. pumps combined with i.v. bolus dosing QD × 7.

An experiment was performed to compare continuous infusion with bolus dosing. As shown below in Table 4, three IL-2 concentrations were administered via continuous infusion or bolus dosing and the results compared. It is apparent from Table 4 that bolus dosing was less toxic and more efficacious than continuous infusion. These results were confirmed in an a rat fibrosarcoma model.

TABLE 4

| Group | No. Deaths/No. Treated | % TGI | Cures |
|---|---|---|---|
| 1.2 mg/kg/D | | | |
| CI | 1/14 | 81% | 1/13 |
| Bolus | 0/15 | 90% | 4/15 |
| 0.6 mg/kg/D | | | |
| CI | 3/15 | 31% | 0/12 |
| Bolus | 0/15 | 60% | 1/15 |
| 0.3 mg/kg/D | | | |
| CI | 0/15 | 21% | 0/15 |
| Bolus | 0/15 | 38% | 1/15 |

* Continuous IP infusion results in a reduced therapeutic index compared to IP bolus dosing in Meth A.

EXAMPLE 2

Unmodified IL-2 and PEG (7,000 MW) modified IL-2 (having an apparent molecular weight of 160 kD) were administered to mice who were transplanted with one of three tumor types; Meth A; B 16 melanoma; and Pan-02. The details are more specifically set out in Zimmerman et al., 1989, *Cancer Research*, 49:6521–6528 which is hereby incorporated by reference in its entirety.

A. Schedule Dependence in Meth A:

The Meth A model was investigated initially because it was known to be sensitive to IL-2 under a variety of protocols, probably due to the tumor's immunogenic nature. Table 5(A) presents the results of dose-response studies in which unmodified IL-2 was given i..v. once daily for 9 days (QD×9). The maximum dose administered was 12.5 mg/kg/dose (112.5 mg/kg total dose) due to solubility limitations of the IL-2 and iv dosing volume restrictions. This dose level was near the maximum tolerated dose, however, as 1/10 hosts died due to treatment. Complete regressions at the s.c. site of injection were obtained in 3/10 and 4/10 of the animals in the 2 highest dose groups. Further, there were modest dose-dependent anti-tumor effects observed at the 2 lower dose levels, as shown by the TIC % (Table 5(A)).

PEG modified IL-2 (160 kD apparent molecular weight) was also administered to the mice. As shown in Table 5(B), four different treatment schedules were used: Q7D×2, Q4D×3, Q3D×4, and Q2D×5. The 3 total dose levels of 50, 25 or 12.5 mg/kg PEG-IL-2 were based on preliminary single dose studies. A single i.v. dose of PEG-IL-2 at 50, 25 or 12.5 mg/kg was lethal in 5/5, 2/5, or 0/5 Meth A bearing mice, respectively. When these same total doses were divided and delivered by the various schedules, the toxicity of the treatments was schedule dependent. At 50 mg/kg total PEG-IL-2, toxicity was observed only on the Q7D×2 and Q2D×5 schedules. The other combinations of dose and schedule were not lethal, with the exception of the 25 mg/kg dose on the Q2D×5 schedule (Table 5(B)). As discussed below, this dependence on the frequency of administration to produce the lethality is related to the minimum plasma concentration of L-2 attained between doses (i.e., the trough).

FIG. 3 (A–D) graphically depicts the pharmacokinetics of PEG-IL-2 in mice dosed i.v. with 25 mg/kg (total dose) on the four schedules discussed above for the Meth A model. IL-2 bioactivity is expressed in I.U./ml plasma. FIG. 3(A) shows the Q7D×2 schedule (12.5 mg/kg/dose); FIG. 3(B) shows the Q4D×3 schedule (8.33 mg/kg/dose); FIG. 3(C) shows the Q3D×4 schedule (6.25 mg/kg/dose); and FIG. 3(D) shows the Q2D×5 schedule (5 mg/kg/dose).

TABLE 5(A)

IL-2 Anti-Tumor Efficacy in Meth A

| Total IL-2 dose (mg/kg)[a] | T/C %[b] | Number deaths/ total treated[c] | Complete regressions[d] |
|---|---|---|---|
| 112.5 | 6.9[e] | 1/10 | 4/9[e] |
| 90 | 5.3[e] | 0/10 | 3/10[e] |
| 45 | 22.0[e] | 0/15 | 0/15 |
| 9 | 66.2[e] | 0/10 | 1/10 |

TABLE 5(B)

PEG-IL-2 Anti-Tumor Efficacy in Meth A

| Total PEG-IL-2 dose (mg/kg)[f] | Schedule | T/C % | No. deaths/ total treated | Complete regressions |
|---|---|---|---|---|
| 50 | Q7D × 2 | 49[e] | 4/10[e] | 5/6[e] |
| 25 | | 7.6[e] | 0/10 | 8/10[e] |
| 12.5 | | 17.9[e] | 0/10 | 3/10[e] |
| 50 | Q4D × 3 | 17.4[e] | 0/10 | 2/10 |
| 25 | | 23.9[e] | 0/10 | 2/10 |
| 12.5 | | 56.3[e] | 0/10 | 0/10 |
| 50 | Q3D × 4 | 7.6[e] | 0/5 | 0/5 |
| 25 | | 10.5[e] | 0/5 | 2/5[e] |
| 12.5 | | 14.1[e] | 0/5 | 2/5[e] |
| 50 | Q2D × 5 | — | 5/5[e] | — |
| 25 | | — | 5/5[e] | — |
| 12.5 | | 20.3[e] | 0/5 | 0/5 |

[a]Therapy was initiated 7 days after tumor implant, i.v., daily for 9 days. Five animals/group/experiment.
[b]T/C % calculated as the mean tumor volume of treated animals on day 21/mean tumor volume of control animals on day 21, × 100.
[c]Treatment-caused deaths.
[d]Complete regressions at the s.c. site of tumor inoculation were assessed on day 35. No spontaneous regressions were observed in controls.
[e]Significantly different compared to control groups by Quade Rank Analysis of Covanance, p set at 0.05.
[f]PEG-IL-2 was administered i.v. starting 7 days after tumor inoculation, on the schedules shown. The doses were appropriately divided in order to deliver the same total dose on the various schedules.

B. Schedule Dependence in B16:

The B16 model was not very sensitive to unmodified IL-2 treatment, even at lethal doses, as shown in Table 6(A). As in the Meth A studies, the maximum i.v. dose achievable was 112.5 mg/kg total IL-2 on the QD×9 schedule; however in this case, 6/16 animals died at this dose level. The $BDF_1$ mice used for B16 were more sensitive to IL-2 than the Balb/c Meth A hosts at all but the lowest dose; 1/16, 5/16, and 6/16 died at 45, 90, 112.5 mg/kg, respectively. Even at these toxic levels there were no complete regressions obtained in the B16 tumors, and only a small mean increase of 3.5 days in the tumor growth delay parameter (T-C) was obtained at the highest dose (Table 6(A)).

The anti-tumor efficacy of PEG-IL-2 was studied at 3 dose levels, 18, 12, or 6 mg/kg total dose. These levels were lower than those studied in Meth A because of the increased sensitivity of the $BDF_1$ hosts to its lethal effects, as noted above. As shown in Table 6(B), the toxicity of the treatments was again schedule dependent, in a manner similar to that observed in Meth A. The Q7D×2 schedule did not produce lethality at these doses; however, there was a clear dose-dependent lethality associated with either the Q4D×3 or the Q3D×4 schedule. A single experiment at 30 mg/kg also produced no lethality on the Q7D×2 schedule, but no greater efficacy than with 18 mg/kg was obtained. Further studies are ongoing in this model to more fully establish the doses and length of treatment which produce the maximum therapeutic benefit.

The efficacy of the PEG-IL-2 on the Q7D×2 schedule at non-toxic doses was superior to that obtained with unmodified IL-2 even when IL-2 was administered at toxic levels, as shown in Table 6(B) by the tumor growth delay parameter, T-C. For example, at 18 mg/kg, a tumor growth delay of 13.6 days was obtained (Table 6(B)), which corresponded to a mean tumor growth inhibition of ≥95% compared to controls at day 28 post-implant. In addition, the third experiment in this series resulted in a complete block of tumor growth in 3/6 mice treated at 18 mg/kg that was durable through day 64, the final day of observation.

TABLE 6(A)

Anti-Tumor Efficacy in B16 Melanoma

| Total rhIL-2 dose (mg/kg)[a] | T - C (days)[b] | Number deaths/ total treated[c] |
|---|---|---|
| 112.5 | 3.5 | 6/16[d] |
| 90 | 2.9 | 5/16[d] |
| 45 | 2.6 | 1/16 |
| 9 | 1.5 | 0/16 |

TABLE 6(B)

PEG-IL-2 Anti-Tumor Efficacy in B16 Melanoma

| Total PEG-IL-2 dose (mg/kg)[e] | Schedule | T - C (days) | Number deaths/ total treated |
|---|---|---|---|
| 18 | Q7D × 2 | 13.6[d,f] | 0/16 |
| 12 |  | 10.0[d] | 0/16 |
| 6 |  | 8.1[d] | 0/16 |
| 18 | Q4D × 3 | ND[g] | 9/10[d] |
| 12 |  | 10.1[d] | 1/10 |
| 6 |  | 7.2[d] | 0/10 |
| 18 | Q3D × 4 | — | 10/10[d] |
| 12 |  | — | 10/10[d] |
| 6 |  | 7.2[d] | 6/10[d] |

[a]IL2 was administered QD × 9, i.v., beginning 1 day after s.c. tumor implant. Five animals/group in 2 experiments, 6 animals/group in the third experiment.
[b]T - C is the tumor growth delay, determined as the mean number of days for the treated tumor volume to reach 500 mm$^3$ minus the mean number of days for the control tumor volumes to reach 500 mm$^3$. Mean value given for 3 experiments.
[c]Treatment-caused deaths.
[d]Significantly different than controls, as in Table 1.
[e]PEG-IL2 was given iv starting one day after sc tumor implant.
[f]Three of six mice in the third experiment had a complete block of tumor growth through the last day of observation, day 64. These mice were excluded from the calculation of T - C.
[g]Not determined due to excessive toxicity of treatment.

C. Schedule Dependence in Pan-02:

As a single agent, IL-2 produced limited anti-tumor efficacy against Pan-02 even at toxic levels when benefit was measured by either of two parameters (see Table 7(A)).

The 3 doses of PEG-IL-2 used in the Pan-02 model were 12, 6, or 3 mg/kg, as shown in Table 7(B). Although the toxicity of PEG-IL-2 was reduced at these dose levels compared to those used in the B16 model, there was a schedule-dependent increase in toxicity as the interval between doses was decreased. No deaths were recorded on the Q7D×2 schedule, 1/30 mice died on Q4D×3, 5/30 died on Q3D×4, and 10/15 died on the 3 doses of the Q2D×5 schedule (Table 7(B)). An additional single study has shown that PEG-IL-2 at 24 mg/kg on the Q7D×2 schedule also was not lethal.

The anti-tumor efficacy obtained with PEG-IL-2 was not markedly dependent on the schedule of administration, in contrast to the results obtained with the other 2 models. The activity observed at non-lethal doses with PEG-IL-2, however, was again superior to that obtained with unmodified IL-2 at lethal doses. At the sc site of tumor implant, the Q7D×2 schedule resulted in about a 5 day mean decrease in the rate of growth to 500 mm$^3$ (range 3.2–5.7 days) when compared to controls (T-C) (p<0.05). The mean T-C on the other schedules ranged from about 1.5 to 4 days at non-lethal doses (Table 7(B)). The Q2D×5 schedule was once again quite toxic, and of limited therapeutic value.

TABLE 7(A)

IL-2 Anti-Tumor Efficacy in Pan-02

| Total IL-2 dose (mg/kg)[a] | T - C (days)[b] | % ILS[c] | Number deaths/ total treated[d] |
|---|---|---|---|
| 112.5 | 0.4 | <100 | 2/5[e] |
| 45 | 0.5 | 143[e] | 0/10 |
| 18 | 0.8 | 127 | 0/5 |

TABLE 7(B)

PEG-IL-2 Anti-Tumor Efficacy in Pan-02

| Total PEG-IL2 dose (mg/kg)[f] | Schedule | T - C (days) | Day of death[g] Median | Day of death[g] Range | % ILS | No. deaths/ Total Treated |
|---|---|---|---|---|---|---|
| 12 | Q7D × 2 | 4.5[e] | 30.0 | 20–>57 | 153[e] | 0/10 |
| 6 |  | 5.7[e] | 31.5 | 20–49 | 163[e] | 0/10 |
| 3 |  | 3.2 | 32.5 | 24–38 | 170[e] | 0/10 |
| 12 | Q4D × 3 | 4.3[e] | 36.5 | 21–45 | 197[e] | 0/10 |
| 6 |  | 1.9 | 32.5 | 23–46 | 170[e] | 1/10 |
| 3 |  | 2.1 | 34.5 | 24–42 | 183[e] | 0/10 |
| 12 | Q3D × 4 | 4.8[e] | 38.0 | 29–49 | 207[e] | 5/10[e] |
| 6 |  | 2.9 | 32.5 | 20–49 | 170[e] | 0/10 |
| 3 |  | 1.6 | 23.5 | 20–40 | 110 | 0/10 |
| 31.2 | Q2D × 5 | — | — | — | — | 5/5[e] |
| 12.5 |  | — | — | — | — | 5/5[e] |
| 2.5 |  | 3.5 | 15.0 | 19–35 | 100 | 0/5 |

[a]IL-2 treatment started 7 days following s.c. tumor implant, i.v., QD × 9. Five mice/group/experiment.
[b]T - C calculated as in Table 2.
[c]% ILS is the percent increase in lifespan: calculated as the median day of death of the treated group/median day of death of the controls, × 100.
[d]Treatment-caused deaths.
[e]Significantly different than controls, as in Table 1.
[f]PEG-IL-2 treatment started 7 days post-implant, i.v., on the schedules indicated.
[g]Tumor-bearing hosts which did not survive treatment were excluded from calculations of survival. Days post-tumor inoculation.

In the Meth A, B16, and Pan-02 tumor models, the anti-tumor efficacy of PEG-IL-2 was found to be superior to that of unmodified IL-2 at equitoxic doses. Further, in these 3 murine tumor models the toxicity and the anti-tumor efficacy of PEG-IL-2 was found to be dependent on the schedule of administration (Tables 5(B), 6(B), 7(B)). The Q7D×2 schedule was the least toxic at the doses studied, and resulted in the best anti-tumor activity. More closely spaced dosing regimens were increasingly toxic as the interval between doses (i.e., the trough) was decreased. Further, no enhancement of the efficacy was obtained by decreasing the interval between doses, and in many instances the anti-tumor activity was reduced in comparison to the Q7D×2 schedule.

Meth A was somewhat sensitive to IL-2, as 3/10 and 4/10 complete regressions were obtained at the 2 highest dose levels. The PEG-IL-2 was more active however, as 8/10 complete regressions were observed at equitoxic, or even less than equitoxic, doses (Table 5(A) and (B)). In B16, which was marginally sensitive to unmodified IL-2 even at lethal dose levels, PEG-IL-2 treatment at non-lethal doses resulted in a 2-fold increase in tumor growth delay (T-C) compared to unmodified IL-2 at lethal doses (Table 6(A) and (3)). If the highest non-lethal doses were compared, an increase of over 9-fold in T-C was obtained with PEG-IL-2 treatment: T-C of 13.6 days for PEG-IL-2 Q7D×2 at 18 mg/kg, compared to 1.5 days for unmodified IL-2 at 9 mg/kg, QD×9. A complete block of tumor growth in 3/16 treated animals was also observed with PEG-IL-2 at this dose. In Pan-02, a tumor resistant to unmodified IL-2 treatment, PEG-IL-2 increased the T-C to as much as 5.7 days (6 mg/kg, Q7D×2). In addition, an increase in the lifespan of the tumor hosts of from 150% to nearly 200% was obtained with PEG-IL-2 treatment at non-lethal doses (Table 7(A) and (B)).

The response of other methylcholanthrene-induced fibrosarcomas and of murine mammary adenocarcinomas to unmodified IL-2, or unmodified IL-2 in combination with LAK cells has been found to correlate with the degree of immunogenicity of the tumor. Meth A has also been shown to be immunogenic, which probably contributed to its sensitivity to unmodified IL-2 and PEG-IL-2. The B16 and Pan-02 tumors apparently are non-immunogenic however, as defined by re-implantation studies and as confirmed by their resistance to unmodified IL-2. The PEG-IL-2 treatments did result in a significant amount of anti-tumor activity, however, which suggested that perhaps even resistant, non-immunogenic tumors could respond to IL-2 if a more optimum manner of therapy was used. It should also be clear that for these more resistant tumors, 2 weekly treatments may not be the most therapeutic schedule possible, but was chosen to match those used in Meth A in order to develop the comparisons made in this series of experiments. Additional weekly treatments might increase the degree of anti-tumor activity obtained in these more resistant models.

In earlier studies with a PEG-IL-2 species modified to a lesser extent than the material used in the present studies, 5 daily i.p. treatments of 80 µg/kg (0.4 mg/kg total dose), resulted in a marked decrease in the growth of Meth A at day 10. Additional investigations revealed that this schedule and route was a comparatively toxic method of PEG-IL-2 administration. Therefore, we began to investigate the protocols described in the present study to establish less toxic and more efficacious regimens. In addition, pharmacokinetic studies have demonstrated that modification of IL-2 with PEG prolonged the half-life in proportion to the degree of modification of the IL-2, and that the clearance can be predicted from the hydrodynamic radii of the modified species. We hypothesized from this work that perhaps different degrees of modification would sufficiently alter the pharmacokinetics such that determination of the protocol with the best therapeutic index would depend on these clearance characteristics. Preliminary in vivo tumor studies comparing a PEG-IL-2 species with apparent molecular weight of 93–95 kD with the results presented here have confirmed these expectations.

The toxicity of PEG-IL-2 is hypothesized to be related to the minimum plasma concentration attained between doses, as illustrated by the striking schedule dependency of PEG-IL-2 toxicity in these studies (Tables 5(B), 6(B), and 7(B)). In addition, the duration of low plasma concentrations also appeared to be important. For example, at 25 mg/kg on the Q7D×2 schedule (a non-toxic regimen in Meth A), the calculated minimum plasma levels reached approximately $6 \times 10^{-5}$ I.U./ml, a theoretical number of questionable biologic significance. In addition however, the interval between which measurable levels (1–10 I.U./ml) could be reliably detected was about 4 days, the longest of the schedules tested (FIG. 3A).

On the Q3D×4 schedule at 18 mg/kg, or 12 mg/kg, toxic deaths were recorded in the B16 (10/10), or Pan-02 (5/10) models, respectively. The minimum plasma levels in this case were approximately 6 I.U./ml, which meant there was no time interval during which the PEG-IL-2 levels were below measurable concentrations (FIG. 3C). The Q2D×5 schedule proved to be essentially 100% lethal; in this case, the lowest levels achieved between doses were about 94 I.U./ml (FIG. 3D).

Further, high single doses of PEG-IL-2 were toxic, which also suggested that the time IL-2 stays above a particular plasma concentration can contribute to toxicity. Data obtained using an unmodified IL-2 with improved solubility have indicated that 75 mg/kg as a single i.v. bolus is not lethal in Meth A tumor bearing Balb/c mice. The clearance of this material is very similar to the unmodified IL-2 shown here. Therefore, these data also support the hypothesis that the peak plasma concentration alone does not determine the toxicity of IL-2, but that the clearance characteristics are also major contributory factors to IL-2 toxicity.

The efficacy obtained is hypothesized to be related to the peak plasma IL-2 concentration, as well as the manner in which the levels fall off, since in all 3 tumor models there was a dose dependence to the efficacy obtained. The Q7D×2 schedule resulted in the best therapeutic index, since there was little or no lethality associated with the treatments, and substantial anti-tumor activity was observed (Tables 5(B), 6(B), and 7(B)). The degree of anti-tumor activity obtained was also schedule dependent, however, which suggested that while higher peak IL-2 concentrations improved the anti-tumor response, the doses had to be delivered at appropriate intervals in order to reduce the toxicity of the treatment. One pharmacokinetic factor that did not appear to be significant was the area under the curve. Since the same total dose was delivered on each of the different schedules, the area under the curve ("AUC") would be equivalent at each dose level.

EXAMPLE 3

An IL-2 formulation was prepared by the method similar to U.S. Pat. No. 4,604,377. A PEG-IL-2 (160 kD apparent molecular weight) was prepared in a manner similar to U.S. Pat. No. 4,766,106.

Four groups of Fisher rats were prepared for the experiment with 4 animals per group as follows:

Group A: IL-2 infusion group—Unmodified IL-2 was delivered by a computer driven infusion pump to simulate the clearance profile of a 1.6 mg/kg i.v. bolus dose of PEG-IL-2. Total IL-2 dose delivered was 38.4 mg/kg over 48 hours.

Group B: sham infusion group—IL-2 excipient infused as in Group A.

Group C: 1.6 mg/kg bolus dose PEG-IL-2 group.

Group D: sham bolus dose group (PEG-IL-2 excipient).

Surgery was performed on all animals in all 4 groups one day prior to the infusions or bolus dose injections. Cannulas were inserted into the femoral vein for infusion and into the jugular vein for blood sampling. Teflon jackets were fitted to the rats to channel the tubing into the pump apparatus and to prevent the animals from dislodging the cannulas. On this same day (one day prior to therapeutic/sham treatment) animals also received fibrosarcoma tumor implants as described below.

The rat fibrosarcoma is a spontaneous solid tumor which is passed as a tumor brei on a bimonthly basis. Tumor brei was maintained frozen in liquid nitrogen in sterile tissue culture medium (RPMI 1640+20% FCS+10% DMSO). A tumor cycle was initiated by thawing a vial of tumor brei and injecting 0.1 ml subcutaneously in the flank of 150 g female Fischer rats. Tumors were passed a minimum of 2 times from frozen before being used in an experiment. A tumor cycle is defined as no greater than 20 passages after which a new vial from the original stock brei is thawed and the cycle restarted. Tumor brei for passage was prepared by excising a 14–18 day tumor, mincing it into ~1 mm$^3$ pieces and implanting 0.1 ml brie SC in the flank.

A computer program controlled the rate of infusion of a Harvard pump (model 22) using a serial port interface. The rate of infusion was calculated as a function of time. The important part of this program was that it read the computer's clock to determine elapsed time, calculated the infusion rate and then sent a rate instruction to the pump. Calculations of infusion rate were controlled by the program. In this case, a rate instruction was sent every 20 seconds. A mathematical function curve for IL-2 infusion produced a plasma concentration-time profile in the rat that was virtually identical to the one obtained for an intravenous bolus injection of PEG-IL-2.

The following day, drug or excipient was administered as described for each group and blood samples were obtained at selected time points 1, 5, 15, 30 minutes, 1, 2, 4, 7, 10, 22, 30, 48 hours over a 48 hour period in order to verify program and delivery accuracy. Samples were stored at −70° and bioassayed.

The effects of therapy on the rat subcutaneous fibrosarcoma were evaluated by measuring tumor volume in 2 perpendicular directions (L×W$^2$)$_2$ at selected times over 21–28×(7, 10, 14+21) days.

Results:

FIG. 4 shows the blood clearance curves for PEG-IL-2 and IL-2 infused by computer program-driven pump. Pharmacokinetic parameters obtained from the data are shown in Table 8. The basic conclusions which can be drawn from this data are that all parameters (initial blood levels, alpha and beta phase half lives and areas under the curves) were not significantly different for PEG-IL-2 and IL-2. Thus, the computer program delivered IL-2 with a pharmokinetic profile similar to that of bolus PEG-IL-2.

TABLE 8

Comparing PK Parameters of IL-2 with PEG IL-2

| | AUC 10$^5$ U/ml-hr | Time 0 Conc. 10$^5$ U/ml | α Half life minutes | β Half life hours |
|---|---|---|---|---|
| PEG-IL-2 (n = 4) | 6.59 ± 0.45 | 2.34 ± 0.47 | 46.7 ± 7.7 | 6.16 ± 0.31 |
| IL-2 (n = 4) | 5.557 ± 0.53 | 3.17 ± 0.45 | 37.8 | 6.668 |
| p value | 0.516 | 0.331 | 0.271 | 0.200 |

* AUC was calculated by trapezoidal rule extrapolated to time infinity.
* Concentration at time 0 was calculated by log linear regression of the first three data points.

Our results showed that 1.0 mg/kg/day ×10 IL-2 was the MTD and that 2.0 mg/kg/day IL-2 was too toxic. Similar efficacy results are seen with single bolus doses of PEG-IL-2 in this same rat tumor model. The anti-tumor efficacy seen in this case is significantly better than IL-2 given for 5 or 10 days and a rough estimate of 20-fold improvement in potency is gleaned from the comparison of total doses of IL-2 and PEG-IL-2 delivered.

FIG. 4 and Table 8 show the results of the present study where IL-2 was administered for 48 hours by computer-driven pump to simulate a single bolus dose of PEG-IL-2. Within the limits of this subcutaneous tumor model, there was no statistically significant difference between a single bolus dose of PEG-IL-2 and IL-2 given by computer-driven infusion pump to obtain IL-2 blood concentrations nearly identical to those obtained with a bolus dose of PEG-IL-2.

Thus, for the same area under the blood clearance curve, the administration of IL-2 with a peak/trough profile similar to that of PEG-IL-2 allows the delivery of 20-fold more IL-2, and improved anti-tumor efficacy, with no incremental toxicity. This result also suggests that the mechanisms) of anti-tumor efficacy are the same or similar for IL-2 and PEG-IL-2.

The present invention has been described with reference to specific embodiments. However, this application is intended to cover those changes and substitutions which may be made by those skilled in the art without departing from the spirit and the scope of amended claims.

We claim:

1. A method for providing IL-2 anti-tumor therapy to a mammalian patient comprising the steps of:
   (a) administering to a mammalian patient in need of treatment a dose of IL-2 such that the plasma concentration of IL-2 in said patient is maintained both above the therapeutic threshold but less than the maximum tolerated dose for 12 to 80 hours;
   (b) allowing the plasma concentration of IL-2 in said patient to decline to below 10 I.U./ml within 48 to 96 hours of commencing IL-2 administration to said patient according to step (a);
   (c) providing said patient with 2½ to 4½ days of abstinence from IL-2 administration; and
   (d) thereafter repeating steps (a)–(c).

2. The method of claim 1 wherein in Step (a) the dose of IL-2 is maintained above the therapeutic threshold but less than the maximum tolerated dose for 24 to 60 hours.

3. The method of claim 2 wherein in Step (b) the plasma concentration of IL-2 in said patient is allowed to decline to below 1.0 I.U./ml within 48 to 96 hours of commencing said IL-2 administration to said patient.

4. The method of claim 2 or 3 wherein the mammalian patient is a human.

5. The method of claim 4 wherein in Step (c) the patient is provided with 3½ to 4½ days of abstinence from IL-2 administration.

6. The method of claim 5 wherein the IL-2 is covalently conjugated to a member selected from the group consisting of polyethylene glycol and polyoxyethylated polyol.

7. The method of claim 6 wherein the IL-2 is recombinant.

8. The method of claim 7 wherein the IL-2 is conjugated to a polyethylene glycol.

9. The method of claim 8 wherein the polyethylene glycol has an average molecular weight of 1,000 to 40,000 daltons.

10. The method of claim 9 wherein the polyethylene glycol has an average molecular weight of 2,000 to 20,000 daltons.

11. The method of claim 10 wherein the polyethylene glycol has an average molecular weight of 3,000 to 12,000 daltons.

12. The method of claim 7 wherein the IL-2 is covalently conjugated to a polyoxyethylated polyol.

13. The method of claim 12 wherein the polyoxyethylated polyol is a member selected from the group consisting of polyoxyethylated sorbitol, polyoxyethylated glucose and polyoxyethylated glycerol.

14. The method of claim 12 wherein the polyoxyethylated polyol is polyoxyethylated glycerol.

15. The method of claim 14 wherein the polyoxyethylated glycerol has an average molecular weight of 1,000 to 40,000.

16. The method of claim 3 wherein the IL-2 is administered intravenously, subcutaneously or intraperitoneally.

17. The method of claim 6 wherein the IL-2 is administered intravenously, subcutaneously, or intraperitoneally.

18. A method for enhancing the therapeutic index of IL-2 treatment in a human patient comprising the steps of:
(a) determining a therapeutic threshold and a maximum tolerated dose of IL-2 for a human patient in need of IL-2 treatment;
(b) administering IL-2 to the patient such that
    (i) the patient's plasma concentration of IL-2 is maintained above the therapeutic threshold but less than the maximum tolerated dose for 12 to 80 hours, and
    (ii) the patient's plasma concentration of IL-2 is allowed to decline to less than or equal to 10 I.U./ml within 48 to 96 hours of commencing said administering of IL-2 to the patient;
(c) providing the patient with at least 3½ days of abstinence from IL-2 administration; and
(d) repeating steps (b) and (c).

19. The method of claim 18 wherein in step (b) (ii) the patient's plasma concentration of IL-2 is allowed to decline to a concentration of IL-2 less than or equal to 1 I.U./ml within 96 hours of commencing administering IL-2 to the patient.

20. The method of claim 18 wherein in step (c) the patient is provided with 3½ to 4½ days of abstinence from IL-2 administration.

21. The method of claim 1 wherein in Step (a) the dose of IL-2 is maintained above the therapeutic threshold for at least 48 hours.

22. The method of claim 21 wherein in Step (b) the patient is provided with 3½ to 4½ days of abstinence from IL-2 administration.

23. The method of claim 18 wherein in Step (b) IL-2 is administered to the patient such that the patient's plasma concentration of IL-2 is maintained above the therapeutic threshold for 24–60 hours.

24. The method of claim 18 wherein in Step (b) IL-2 is administered to the patient such that the patient's plasma concentration of IL-2 is maintained above the therapeutic threshold for at least 48 hours.

25. The method of claim 1, wherein said IL-2 is selected from the group consisting of $Ala_{104}$ $Ser_{125}$ IL-2; des-$Ala_1$ des-$Pro_2$ des-$Thr_3$ des-$Ser_4$ $Ala_{104}$ $Ser_{125}$ IL-2; des-$Ala_1$ des-$Pro_2$ des-$Thr_3$ des-$Ser_4$ des-$Ser_5$ des-$Ser_6$ IL-2; and des-$Ala_1$ $Ser_{125}$ IL-2.

26. The method of claim 25, wherein said IL-2 is des-$Ala_1$ $Ser_{125}$ IL-2.

27. The method of claim 11, wherein said IL-2 is selected from the group consisting of $Ala_{104}$ $Ser_{125}$ IL-2; des-$Ala_1$ des-$Pro_2$ des-$Thr_3$ des-$Ser_4$ $Ala_{104}$ $Ser_{125}$ IL-2; des-$Ala_1$ des-$Pro_2$ des-$Thr_3$ des-$Ser_4$ des-$Ser_5$ des-$Ser_6$ IL-2; and des-$Ala_1$ $Ser_{125}$ IL-2.

28. The method of claim 27, wherein said IL-2 is des-$Ala_1$ $Ser_{125}$ IL-2.

29. A method for providing IL-2 anti-tumor therapy to a human patient comprising the steps of:
(a) administering to a human patient in need of treatment a dose of IL-2 such that the plasma concentration of IL-2 in said patient is maintained both above 100 I.U./ml but less than the maximum tolerated dose for 12 to 80 hours;
(b) allowing the plasma concentration of IL-2 in said patient to decline such that said plasma concentration is below 10 I.U./ml within 48 to 96 hours of commencing IL-2 administration to said patient according to step (a);
(c) providing the patient with 3½ to 4½ days of abstinence from IL-2 administration; and
(d) thereafter repeating steps (a)–(c).

* * * * *